United States Patent [19]

Martin

[11] Patent Number: 4,550,165
[45] Date of Patent: Oct. 29, 1985

[54] PROCESS FOR PRODUCING 1,2,5,6-TETRAHYDRO-4H-PYRROLO-[3,2,1-IJ]-QUINOLIN-4-ONE

[75] Inventor: Pierre Martin, Rheinfelden, Switzerland

[73] Assignee: Ciba Geigy Corporation, Ardsley, N.Y.

[21] Appl. No.: 477,706

[22] Filed: Mar. 22, 1983

[30] Foreign Application Priority Data

Mar. 25, 1982 [CH] Switzerland .......................... 1839/82

[51] Int. Cl.$^4$ .......................................... C07D 471/06
[52] U.S. Cl. ...................................... 546/94; 548/491
[58] Field of Search .......................................... 546/94

[56] References Cited

FOREIGN PATENT DOCUMENTS 1394373  5/1975  United Kingdom .................. 546/94

OTHER PUBLICATIONS

Hayes, R. et al., *J. Chem. Res., Synop.*, (1980), (12), 414–415.
Chupp, J. et al., *J. Het. Chem.*, 16, 65, (1979).
*Chemical Abstracts*, 94: 121279x, (1981).
House, H., *Modern Synthetic Reactions*, 2nd ed., Benjamin/Cummings, Menlo Park, Cal., 1972, pp. 9 and 14.
Hallas, G. et al., *J. Chem. Soc.*, 1518–1519, (1964).
Bass, R. et al., *J. Agr. Food. Chem.* 29, 576–579, (1981).

*Primary Examiner*—Richard A. Schwartz
*Attorney, Agent, or Firm*—Karl F. Jorda

[57] ABSTRACT

There is described a novel process for producing 1,2,5,6-tetrahydro-4H-pyrrolo[3,2,1-ij]-quinolin-4-one (4-lilolidone), usable as fungicide and corresponding to the formula

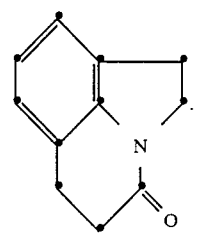

19 Claims, No Drawings

PROCESS FOR PRODUCING 1,2,5,6-TETRAHYDRO-4H-PYRROLO-[3,2,1-IJ]-QUINOLIN-4-ONE

The present invention relates to a process for producing 1,2,5,6-tetrahydro-4H-pyrrolo[3,2,1-ij]-quinolin-4-one, and to novel 5-halo-1,2,3-(1,2-dihydropyrrolo)-4-quinolones which are formed as intermediates during the process.

The 1,2,5,6-tetrahydro-4H-pyrrolo[3,2,1-ij]-quinolin-4-one corresponds to the formula

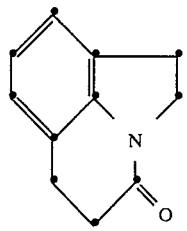
(I)

and is known also under the trivial name of 4-lilolidone. The compound can be used as a systemic fungicide for the protection of cultivated plants, for example rice, against infestation by phytopathogenic microorganisms and thus against plant diseases caused by these microorganisms (cp. G.B. Patent Specification No. 1,394,373).

4-Lilolidone has hitherto been produced by an intramolecular Friedel-Crafts alkylation from N-($\beta$-chloropropionyl)-indoline (cp. J. Chem. Soc. 1518, (1964), G.B. Patent Specification No. 1,394,373 and J. Agric. Food Chem. 29, 576 (1981). A large excess of aluminium chloride, high reaction temperatures or long reaction times are required in this process. The process is disadvantageous also in that the heat of reaction is difficult to remove, and that the separation of by-products and the processing of the final product are very lengthy and complicated. The process is for this reason unsuitable for a profitable production of 4-lilolidone on a commercial scale.

It was therefore the object of the present invention to make 4-lilolidone available in a simple and economical manner, in good yields and with a high degree of purity.

It is suggested according to the present invention that 4-lilolidone be produced by reacting a haloacetylindoline of the formula II

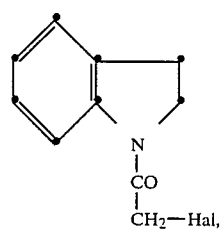
(II)

in which "Hal" is chlorine or bromine, with an addition product formed from an N,N-disubstituted formamide of the formula III

(III)

in which $R_1$ is $C_1$–$C_4$-alkyl or phenyl, and $R_2$ is $C_1$–$C_4$-alkyl, and an acid halide to give a 5-halo-1,2,3-(1,2-dihydropyrrolo)-4-quinolone of the formula IV

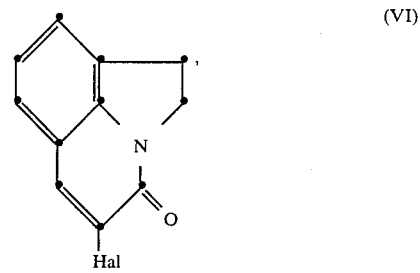
(VI)

in which "Hal" has the meaning defined in the foregoing; and then converting this compound, by catalytic hydrogenation, into 4-lilolidone of the formula I.

The 5-halo-1,2,3-(1,2-dihydropyrrolo)-4-quinolones of the formula IV are novel compounds, and likewise form subject matter of the present invention.

The reaction of a haloacetylindoline of the formula II with the addition product formed from an N,N-disubstituted formamide of the formula III and an acid halide is advantageously performed in an inert solvent. Suitable such solvents are in particular: halogenated aliphatic or aromatic hydrocarbons, such as chloroform, dichloromethane, dichloroethane, carbon tetrachloride, chlorobenzene, dichlorobenzenes, toluene and xylene. It is also possible to use as solvent excess N,N-disubstituted formamide of the formula III, and especially excess acid chloride. Preferred solvents are 1,2-dichloroethane, chloroform and particularly toluene. Especially advantageous is also the use of excess phosphorus oxychloride as solvent.

Acid halides that can be used are in general those which are able to react with an N,N-disubstituted formamide of the formula III to form a Vilsmeier complex. Suitable acid halides are for example: phosphorus trichloride, phosphorus tribromide, phosphorus pentachloride, phosphorus oxychloride, phosphorus oxybromide, phosgene, carbonyl dibromide, carbonyl difluoride, oxalyl chloride, heptachlorobutyric acid chloride, thionyl chloride and thionyl bromide. Also derivatives of some of the aforementioned acid chlorides can be used, for example 2,2,2-trichloro-1,3-dioxa-2-phosphaindane and 2,2-dichloro-1,3-dioxaindane, which can be regarded as derivatives of phosphorus oxychloride and phosgene. Preferred acid halides are phosphorus oxychloride and phosgene.

Suitable N,N-disubstituted formamides of the formula III are for example: N,N-dimethylformamide, N,N-diethylformamide, N,N-dipropylformamide, N,N-dibutylformamide, N-butyl-N-methylformamide and N-methyl-N-phenylformamide (N-formyl-N-methylaniline).

Preferred N,N-disubstituted formamides of the formula II are N,N-dimethylformamide and N-methyl-N-phenylformamide. N,N-Dimethylformamide is especially preferred.

The acid halide is used, when the process is performed in an organic solvent, in an amount of at least 2 mols per mol of N-haloacetylindoline of the formula II. Where the process is carried out in an organic solvent, the acid halide is preferably used in an amount of 2.5–5.0 mols per mol of N-haloacetylindoline of the formula II.

The reaction of a haloacetylindoline of the formula II with the addition product formed from an N,N-disubstituted formamide of the formula III and an acid halide can be performed by firstly producing the addition product from the N,N-disubstituted formamide and the acid halide, and afterwards adding the haloacetylindoline of the formula II. The reaction can however also be carried out by adding the addition product formed from an N,N-disubstituted formamide of the formula III and an acid halide to the haloacetylindoline of the formula II. Furthermore, the reaction can also be advantageously performed by placing a mixture of a haloacetylindoline of the formula II and an N,N-disubstituted formamide of the formula III into the reaction vessel, and introducing the acid halide into this mixture, thus effecting the formation of the addition product from N,N-disubstituted formamide of the formula III and the acid halide in situ.

The reaction temperatures are as a rule between 40° and 100° C. The reaction is generally completed within a few hours. The reaction is particularly advantageously performed at temperatures of between 50° and 75° C., and at these temperatures the reaction time is 1–2 hours. Under these preferred, relatively mild, conditions, the reaction proceeds in general with negligible formation of by-products.

After the reaction of the haloacetylindoline of the formula II with the addition product formed from an N,N-disubstituted formamide of the formula III and an acid halide, the reaction mixture can be further processed in a simple manner, for example by pouring it into aqueous sodium hydroxide solution. There is thus yielded an aqueous suspension of the 5-halo-1,2,3-(1,2-dihydropyrrolo)-4-quinolone of the formula IV, from which the product is easily obtained by filtration and drying. If the reaction of the haloacetylindoline of the formula II with the addition product formed from an N,N-disubstituted formamide of the formula III and an acid halide has been performed in chloroform as solvent, there is obtained, after the pouring of the reaction mixture into aqueous sodium hydroxide solution, a 2-phase mixture in which the required 5-halo-1,2,3-(1,2-dihydropyrrolo)-4-quinolone of the formula IV is present as solution in the organic phase. On removal of the organic phase and evaporation of the solvent the desired 5-halo-1,2,3-(1,2-dihydropyrrolo)-4-quinolone of the formula IV is obtained.

The catalytic hydrogenation of the 5-halo-1,2,3-(1,2-dihydropyrrolo)-4-quinolone of the formula IV, which proceeds with the removal of the 5-halogen, is advantageously performed in an inert organic solvent, and, for neutralising the formed hydrogen halide, in the presence of a base. Suitable inert solvents are in particular: aliphatic and aromatic hydrocarbons, such as cyclohexane, toluene or xylene, as well as lower aliphatic carboxylic acids, particularly acetic acid. Further solvents which can be used are lower alkanols, such as methanol, ethanol and isopropanol. The bases used, in the presence of which the catalytic hydrogenation is carried out, are advantageously hydroxides, carbonates and hydrogen carbonates of alkali metals and alkaline earth metals, and also ammonia or amines. Also alkali metal acetates, especially sodium acetate, can be used as bases.

There may be mentioned as further bases, in the presence of which the catalytic hydrogenation of the 5-halo-1,2,3-(1,2-dihydropyrrolo)-4-quinolones of the formula IV can be carried out, for example: sodium hydroxide, potassium hydroxide, ammonia, triethylamine and pyridine.

Suitable as catalysts for the catalytic hydrogenation of the 5-halo-1,2,3-(1,2-dihydropyrrolo)-4-quinolones of the formula IV are noble metals of the group VIII of the periodic system, particularly nickel, palladium and platinum. The catalysts are used in a very finely divided form, for example as Raney nickel, or on a carrier, for example palladium on charcoal, or platinum on charcoal.

The catalytic hydrogenation of the 5-halo-1,2,3-(1,2-dihydropyrrolo)-4-quinolone of the formula IV is performed as a rule under normal pressure or under a slightly elevated pressure. Catalytic hydrogenation is carried out in practice advantageously under pressures of 1–20 bar, preferably 3–10 bar.

The temperatures at which catalytic hydrogenation can be performed are in general between room temperature and 130° C. Temperatures of 40°–75° C. have proved to be particularly advantageous.

After completion of hydrogenation, further processing of the reaction mixture comprises filtering off the catalyst and evaporating off the solvent.

It is possible with the process according to the invention to produce 4-lilolidone, starting with haloacetylindolines of the formula II, in a yield of about 90% of theory. The process is easy to carry out, and is therefore well suited also for production of 4-lilolidone on a commercial scale. The haloacetylindolines of the formula II, required as starting material, can be produced in a simple manner, commencing with indoline, by reaction thereof with haloacetyl halides, especially haloacetyl chloride, or by reaction of indole with haloacetyl chloride, and catalytic hydrogenation of the N-haloacetylindole obtained.

The process according to the invention is further illustrated by the following Examples.

EXAMPLE 1

(a) Production of 5-chloro-1,2,3-(1,2-dihydropyrrolo)-4-quinolone 19.55 g (0.1 mol) of N-chloroacetylindoline are added portionwise to a mixture of 150 ml (251.2 g; 1.64 mols) of phosphorus oxychloride and 20 ml (19.0 g; 0.26 mol) of N,N-dimethylformamide. After the addition of the N-chloroacetylindoline is completed, the mixture is heated for 1.75 hours at 70°–75° C. internal temperature. The unreacted phosphorus oxychloride is afterwards evaporated off at 40° C. under reduced pressure. The residue is poured into cold sodium hydroxide solution (10%), upon which the product precipitates. After a stirring time of 1 hour, the precipitate is filtered off and dried. The yield is 20.05 g (97.8% of theory) of 5-chloro-1,2,3-(1,2-dihydropyrrolo)-4-quinolone in the form of a beige powder; melting point: 190°–192° C.:

IR spectrum (CHCl$_3$): 1660, 1640 (CO, C=C)cm$^{-1}$. H$^1$-NMR spectrum (100 MHz, CDCl$_3$): 3.33 (broad t, 2H), 4.30 (broad t, 2H), 6.95–7.30 (m, 3H), 7.85 (s, 1H) ppm. $^{13}$C-NMR spectrum (CDCl$_3$: 156.6, 141.3, 130.4, 123.7, 116.5, 47.8 and 27.3 (all s), as well as 134.7, 125.1, 123.8 and 122.8 (all d) ppm.

The phosphorus oxychloride which was evaporated off is pure and can be used again. The N-chloroacetylindoline required as starting material is produced, in the usual manner, from indoline and chloroacetyl chloride; melting point: 129°–130° C.

(b) Production of 4-lilolidone 20.0 g (0.097 mol) of 5-chloro-1,2,3-(1,2-dihydropyrrolo)-4-quinolone are dissolved with 8.0 g of sodium acetate in 200 ml of glacial acetic acid, and, after the addition of 2.0 g of palladium on charcoal (5%), the mixture is hydrogenated at 70° C. under 4 bar. The absorption of hydrogen ceases after 3 hours. The catalyst is filtered off, and subsequently washed on the filter with glacial acetic acid. The filtrate is concentrated by evaporation, and the residue is taken up in ethyl acetate, washed with water, dried over magnesium sulfate and concentrated by evaporation. The yield is 15.3 g (91% of theory) of 4-lilolidone in the form of a white crystalline powder, the entire physical data of which is in agreement with the relevant data in the literature.

EXAMPLE 2

(a) Production of 5-chloro-1,2,3-(1,2-dihydropyrrolo)-4-quinolone 19.55 g (0.1 mol) of N-chloroacetylindoline is introduced portionwise into a solution of 40.0 g (0.26 mol) of phosphorus oxychloride and 19.0 g (0.26 mol) of N,N-dimethylformamide in 150 ml of chloroform. After the addition of N-chloroacetylindoline is completed, the mixture is heated for 24 hours at the reflux temperature. The reaction mixture is afterwards further processed by the injection of (10%) sodium hydroxide solution, separation of the aqueous phase and removal of the chloroform by evaporation. There are obtained 12.5 g (61% of theory) of 5-chloro-1,2,3-(1,2-dihydropyrrolo)-4-quinolone, m.p. 190°–192° C.

EXAMPLE 3

Production of 5-chloro-1,2,3-(1,2-dihydropyrrolo)-4-quinolone 40 g (0.4 mol) of phosgene are introduced at 35° C. into a solution of 14.6 g (0.2 mol) of N,N-dimethylformamide in 70 ml of 1,2-dichloroethane. There are subsequently added portionwise 19.55 g (0.1 mol) of N-chloroacetylindoline, and stirring is maintained at 65° C. for 2 hours. The reaction mixture is then poured onto ice and neutralised with sodium hydroxide solution; the 1,2-dichloroethane is afterwards distilled off, and the precipitate is filtered off and dried. The yield is 18.9 g (92% of theory) of 5-chloro-1,2,3-(1,2-dihydropyrrolo)-4-quinolone, m.p. 191°–192° C.

EXAMPLE 4

19.0 g (0.26 mol) of N,N-dimethylformamide are added dropwise at 25°–30° C., in the course of 1 hour, to 190 g (2.28 mols) of thionyl chloride. There are subsequently added 19.55 g (0.1 mol) of N-chloroacetylindoline, and the mixture is stirred at 60° C. for 3 hours. The excess thionyl chloride is afterwards distilled off at 40° C. under reduced pressure; the residue is stirred up with 200 g of ice and neutralised with sodium hydroxide solution. The yield after filtration and drying is 8.6 g (42% of theory) of 5-chloro-1,2,3-(1,2-dihydropyrrolo)-4-quinolone, m.p. 190°–192° C.

What is claimed is:

1. A process for producing 1,2,5,6-tetrahydro-4H-pyrrolo[3,2,1-ij]-quinolin-4-one, which process comprises reacting a haloacetylindoline of the formula II

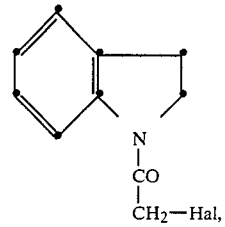

in which "Hal" is chlorine or bromine, with an addition product formed from an N,N-disubstituted formamide of the formula III

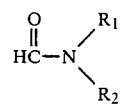

in which $R_1$ is $C_1$–$C_4$-alkyl or phenyl, and $R_2$ is $C_1$–$C_4$-alkyl, and an acid halide to give a 5-halo-1,2,3-(1,2-dihydropyrrolo)-4-quinolone of the formula IV

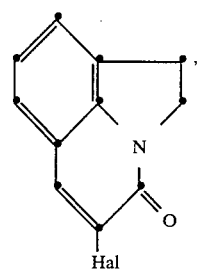

in which "Hal" has the meaning defined in the foregoing; and then converting this compound, by catalytic hydrogenation, into 4-lilolidone of the formula I

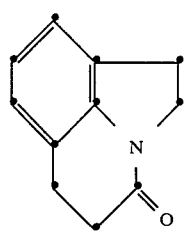

2. A process according to claim 1, wherein the reaction of the haloacetylindoline of the formula II with the addition product formed from an N,N-disubstituted formamide of the formula III and an acid halide is performed in the presence of an inert solvent.

3. A process according to claim 2, wherein the reaction of the haloacetylindoline of the formula II with the addition product formed from an N,N-disubstituted formamide of the formula III and an acid halide is performed in 1,2-dichloroethane, chloroform or toluene as solvent.

4. A process according to claim 2, wherein the reaction of the haloacetylindoline of the formula II with the addition product formed from an N,N-disubstituted formamide of the formula III and an acid halide is performed in excess phosphorus oxychloride as solvent.

5. A process according to claim 1, wherein the acid halide used is selected from the group comprising: phosphorus trichloride, phosphorus tribromide, phosphorus pentachloride, phosphorus oxychloride, phosphorus oxybromide, phosgene, carbonyl dibromide, carbonyl difluoride, oxalyl chloride, heptachlorobutyric acid chloride, thionyl chloride, thionyl bromide, 2,2,2-trichloro-1,3-dioxa-2-phosphaindane or 2,2-dichloro-1,3-dioxaindane.

6. A process according to claim 1, wherein the acid halide used is phosphorus oxychloride or phosgene.

7. A process according to claim 1, wherein the employed N,N-disubstituted formamide of the formula III is N,N-dimethylformamide or N-methyl-N-phenylformamide.

8. A process according to claim 1, wherein the reaction of a haloacetylindoline of the formula II with the addition product formed from an N,N-disubstituted formamide of the formula III and an acid halide is performed by firstly producing the addition product from the N,N-disubstituted formamide and the acid halide, and afterwards adding the haloacetylindoline of the formula II.

9. A process according to claim 1, wherein the reaction of a haloacetylindoline of the formula II with the addition product formed from an N,N-disubstituted formamide of the formula III and an acid halide is performed by adding the addition product formed from the N,N-disubstituted formamide of the formula III and the acid halide to the haloacetylindoline of the formula II.

10. A process according to claim 1, wherein the reaction of a haloacetylindoline of the formula II with the addition product formed from an N,N-disubstituted formamide of the formula III and an acid halide is performed by placing a mixture of a haloacetylindoline of the formula II and an N,N-disubstituted formamide of the formula III into the reaction vessel, and then introducing the acid halide into this mixture.

11. A process according to claim 1, wherein the reaction of a haloacetylindoline of the formula II with the addition product formed from an N,N-disubstituted formamide of the formula III and an acid halide is performed at a temperature of between 40° and 100° C.

12. A process according to claim 11, wherein the reaction of a haloacetylindoline of the formula II with the addition product formed from an N,N-disubstituted formamide of the formula III and an acid halide is performed at a temperature of between 50° and 75° C.

13. A process according to claim 1, wherein there are used, when the process is performed in an organic solvent, at least 2 mols of acid halide per mol of N-haloacetylindoline.

14. A process according to claim 13, wherein there are used 2.5–5 mols of acid halide per mol of N-haloacetylindoline of the formula II.

15. A process according to claim 1, wherein the catalytic hydrogenation of the 5-halo-1,2,3-(1,2-dihydropyrrolo)-4-quinolones of the formula IV is performed in the presence of a noble metal of the group VIII of the periodic system.

16. A process according to claim 15, wherein the catalytic hydrogenation of the 5-halo-1,2,3-(1,2-dihydropyrrolo)-4-quinolones of the formula IV is performed in the presence of nickel, palladium or platinum as catalyst.

17. A process according to claim 1, wherein the catalytic hydrogenation of the 5-halo-1,2,3-(1,2-dihydropyrrolo)-4-quinolones of the formula IV is performed in an inert organic solvent and in the presence of a base.

18. A process according to claim 1, wherein the catalytic hydrogenation of the 5-halo-1,2,3-(1,2-dihydropyrrolo)-4-quinolones of the formula IV is performed under a pressure of 1–20 bar and at a temperature of between room temperature and 130° C.

19. A process according to claim 1, wherein the catalytic hydrogenation of the 5-halo-1,2,3-(1,2-dihydropyrrolo)-4-quinolones of the formula IV is performed under a pressure of 3–10 bar and at a temperature of 40°–75° C.

* * * * *